United States Patent [19]

Schultz

[11] Patent Number: 5,029,592

[45] Date of Patent: Jul. 9, 1991

[54] MULTI-PLANE FORCE TRANSDUCER HEAD FOR AN ISOMETRIC MUSCLE TESTING APPARATUS

[76] Inventor: David R. Schultz, 2860 Pinole Valley Rd., Ste. C, Pinole, Calif. 94564

[21] Appl. No.: 299,234

[22] Filed: Jan. 23, 1989

[51] Int. Cl.⁵ .............................................. A61B 5/22
[52] U.S. Cl. ...................................... 128/774; 73/379
[58] Field of Search .......................... 128/774; 73/379; 272/125, 134

[56] References Cited

U.S. PATENT DOCUMENTS

| | | | |
|---|---|---|---|
| 3,174,343 | 3/1965 | Kusalis | 73/379 |
| 3,374,675 | 3/1968 | Keropian | 73/379 |
| 3,670,573 | 6/1972 | Kroemer | 73/379 |
| 3,752,144 | 8/1973 | Weigler, Jr. | 128/2 S |
| 4,702,108 | 10/1987 | Amundsen et al. | 73/379 |
| 4,732,038 | 3/1988 | DelGiorno et al. | 73/379 |
| 4,742,832 | 5/1988 | Kauffmann et al. | 128/774 |
| 4,805,455 | 2/1989 | DelGiorno et al. | 73/379 |
| 4,824,103 | 4/1989 | Smidt | 272/125 |

Primary Examiner—Kyle L. Howell
Assistant Examiner—Kevin Pontius
Attorney, Agent, or Firm—Donald L. Beeson

[57] ABSTRACT

A transducer head for a muscle testing apparatus has at least two and preferably three pressure test pads situated in three different test planes whereby different directional forces can be applied to the transducer head without the need to adjust its angular orientation. The test pads are mounted on anti-shear arms within the transducer housing so that the forces on the test pads can be transmitted to transducer elements within the housing about a remote shear arm pivot axis. In the preferred embodiment, only two transducer elements are required, one for two opposing test pads, and one for a front test pad in a test plane perpendicular to the test planes for the two opposed test pads. An optional pull device, which projects from the transducer head housing, is attached to one of the anti-shear arms such that the transducer element associated wih that shear arm is responsive to a pulling force on the pull device as well as a pushing force on the associated pressure test pad.

23 Claims, 8 Drawing Sheets

MULTI-PLANE FORCE TRANSDUCER HEAD FOR AN ISOMETRIC MUSCLE TESTING APPARATUS

BACKGROUND OF THE INVENTION

The present invention generally relates to isometric muscle testing apparatus used for testing the performance of different body parts of a human subject, and particularly to the transducer mechanism for the apparatus which acts to generate and send to a monitoring device an electrical signal which is proportionate to a physical force applied to the transducer.

Muscular and neuromuscular disorders can be diagnosed by a qualified health professional using various developed procedures for testing individual muscles or muscle groups. The types of testing procedures developed for this purpose can be divided into three general categories: isometric, isokinetic, and isotonic. Generally, these testing procedures require the stabilization of the patient's body, instructing the patient to exert a force by a limb or other body part against a reacting force in a prescribed manner which isolates the muscle or muscle groups being tested, and sensing the force being exerted. For example, an isometric testing procedure for testing the left lateral deltoid muscle, calls for the patient, while in a sitting position to hold his or her arm out in a horizontal position, bent at the elbow, and to push upwardly with the upper arm against a counter-resisting force applied above the elbow.

Muscle testing procedures were initially developed to be practiced manually: the health professional would grip or hold his or her hand against the patient's limb or body part being tested, instruct the patient to exert a force by that limb or body part in a specified manner, and apply the required counterforce while subjectively sensing the amount of pressure being exerted by the patient. From manual sensation of exerted pressures, a diagnosis would be made, for example, from a sensed pattern of weakness in a muscle or muscle group, or an imbalance between the same muscles on the left and right side of the body.

Because of the subjectivity of manual muscle testing techniques, mechanical muscle testing machines have been devised which sense and provide an objective record of the force exerted by the patient. Examples of such equipment are disclosed in U.S. Pat. Nos. 3,374,675, to Michael Keropian; 3,752,144 to Keith E. Weigle, Jr.; and 4,732,038 to Daniel Del Giorno, et al. The foregoing patents disclose isometric muscle testing machines having a force sensing transducer device held on an upright frame and adjustment mechanisms for positioning the transducer to different heights and angles as required by the health professional. Such testing machines are relatively difficult and time consuming to use in that the angle of the force sensing transducer must, normally, repeatedly be readjusted in the course of a single testing session. Also, proper use of the apparatus normally calls for the recording of each transducer head angle.

The present invention provides a transducer head for a muscle testing apparatus which for most test procedures eliminates the need for any adjustment of the force sensing element used for the test other than an easily made height adjustment. The invention also provides a transducer head which, within a single height adjustable unit, can be used for a wide variety of tests, namely, test procedures requiring pushing forces, tests requiring a pull force, and grip strength tests. The invention further provides a transducer design wherein relatively inexpensive transducer elements can be employed and wherein a variety of electronic options can be provided within a single adjustable unit.

SUMMARY OF THE INVENTION

Briefly, the present invention provides a force transducer head for an isometric testing machine which has at least two pressure test pads in different test planes whereby the transducer head can responsively receive a pushing force from a patient from any one of two different directions without readjustment of the head. In the illustrated embodiment, the transducer head of the invention is provided with three separate test pads in three different test planes, two of the test planes being opposed parallel planes, and the third test plane intersecting to the two parallel test planes, preferably at substantially perpendicular angles. In this illustrated embodiment, a prescribed pushing force can be applied to the single vertically adjustable transducer head from any one of three different directions. Specifically, the three pressure test pads accessibly project from the top, front, and bottom walls of the transducer head housing so as to receive, respectively, a downward directed force, an upward directed force, and a laterally directed force. In a further aspect of the invention, a pull device is optionally provided such that a prescribed pulling force as well as different directional pushing forces can be exerted on the transducer head.

Test pad mounting structures in the transducer housing hold the pressure test pads in their different test planes and act to transmit the applied forces to a transducer means, also in the housing. The transducer means generates and sends to a monitoring device an electrical signal proportionate to forces applied to the pressure pads and optional pull device.

In the preferred embodiment, the mounting structure for each of the separate test pads is comprised of an anti-shear arm having a distal end to which the associated pad is mounted and a proximate end attached to a pivot axis, preferably a hinge axis, at the end of the housing remote from the test pad. To provide good lateral stability to the anti-shear arm, and hence to the test pad mounted thereto, the anti-shear arm's hinge axis is preferably provided by a piano hinge and is formed of a relatively broad extender plate having a generally U-shape construction. As will be understood from the following detailed description of the illustrated embodiment, the anti-shear arms will readily transmit pushing forces normal to the test pads to the transducer means without transmitting lateral or shear forces that may be exerted against the pad. In this manner, construction of the transducer means in the housing does not require relatively expensive transducers that are constructed to protect the transducer load cell from damage caused by shear forces. Use of a hinged arm also insures that the forces against the test pads are transmitted to the transducer means without having to overcome the spring tension of an unhinged extension arm. It is found that this results in more accurate operation of the transducer means.

In respect to the optional pull device, it is contemplated that the pull device will be attached to one of the anti-shear arms holding one of the test pads such that a pulling force on the pull device will be transmitted to the transducer means without the need to add additional transducer elements.

It is specifically contemplated that in the preferred embodiment the transducer means of the invention will be comprised of only two transducer elements to accommodate three separate test pads and the optional pull device. In the illustrated embodiment, a first transducer element is responsively connected to the test pad associated with the front wall of the transducer housing and a second transducer element is connected between the opposed test pads in the housing's opposed top and bottom walls. Also in the illustrated embodiment, the pull device projects from the top wall of the housing and is secured within the housing to the anti-shear arm associated with the bottom wall test pad such that the second transducer element between the opposed top and bottom test pads is also responsive to a pull force on this pulling device.

In yet a further aspect of the invention, the transducer head itself is supported on a support column by means of a hinge support means whereby the angular position of the transducer head, and therefore the orientation of the different test planes of the head, can be adjusted. The transducer head might also be rotated to change the attitude of the pull device, for example, from an upward pull to a horizontal pull.

It is therefore seen that a primary object of the invention is to provide a transducer head for an isometric muscle testing apparatus which presents, in a single unit, multiple transducer test planes without the need to adjust the angular position of the transducer head. It is a further object of the invention to provide a transducer head, which in a single unit, will accommodate a number of different muscle testing procedures requiring that both pushing forces and a pulling forces be exerted by the subject being tested. It is still a further object of the invention to provide a transducer head which is compact, relatively cost efficient to manufacture, and which is aesthetically appealing. Further objects of the invention will become apparent from the following description of the detailed embodiment of the invention.

DETAILED DESCRIPTION OF THE ILLUSTRATED EMBODIMENT

Figure 1:
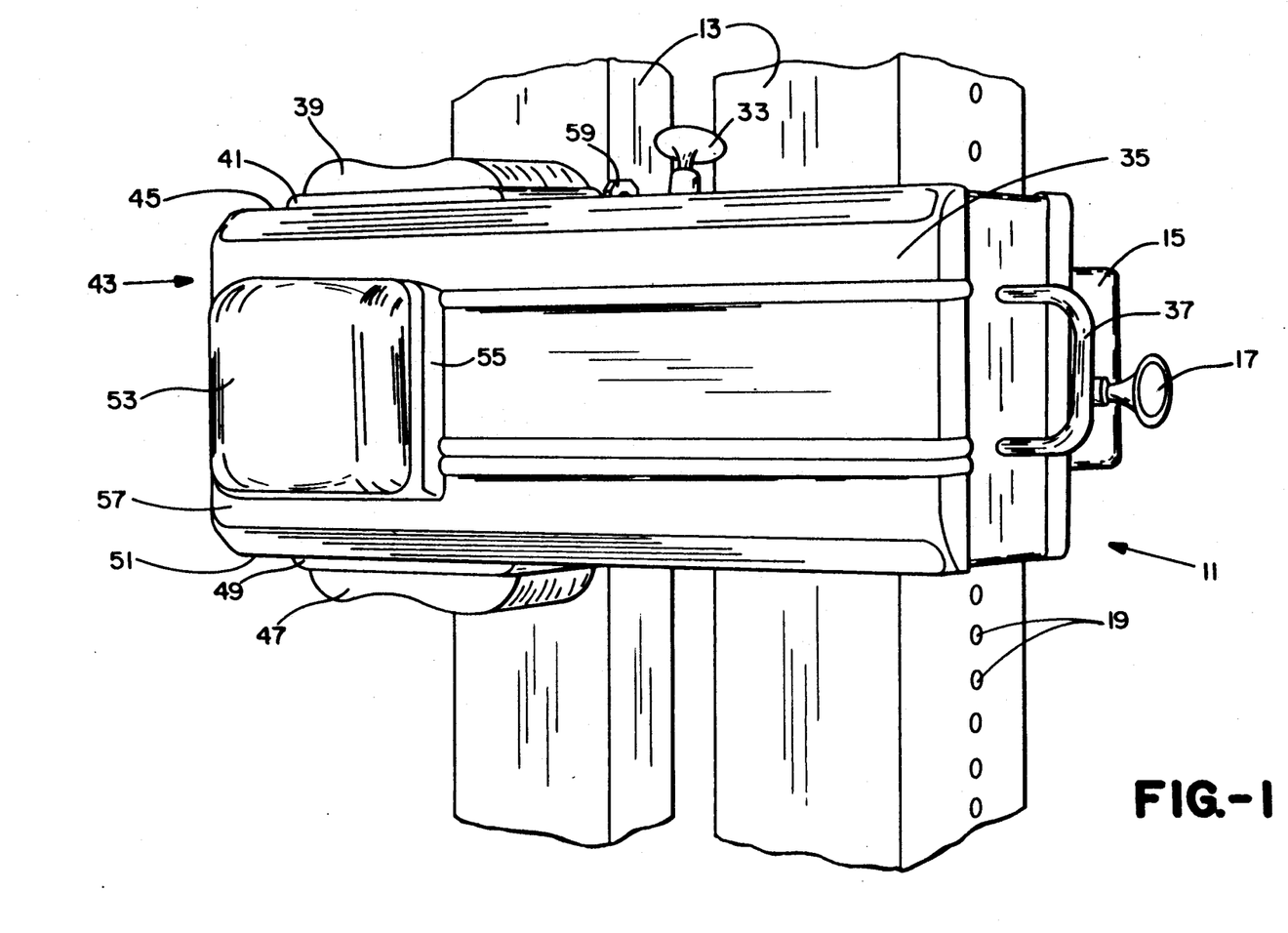
FIG. 1 is a perspective view of a transducer head in accordance with the invention adjustably mounted to vertical head support columns.
Figure 1A:
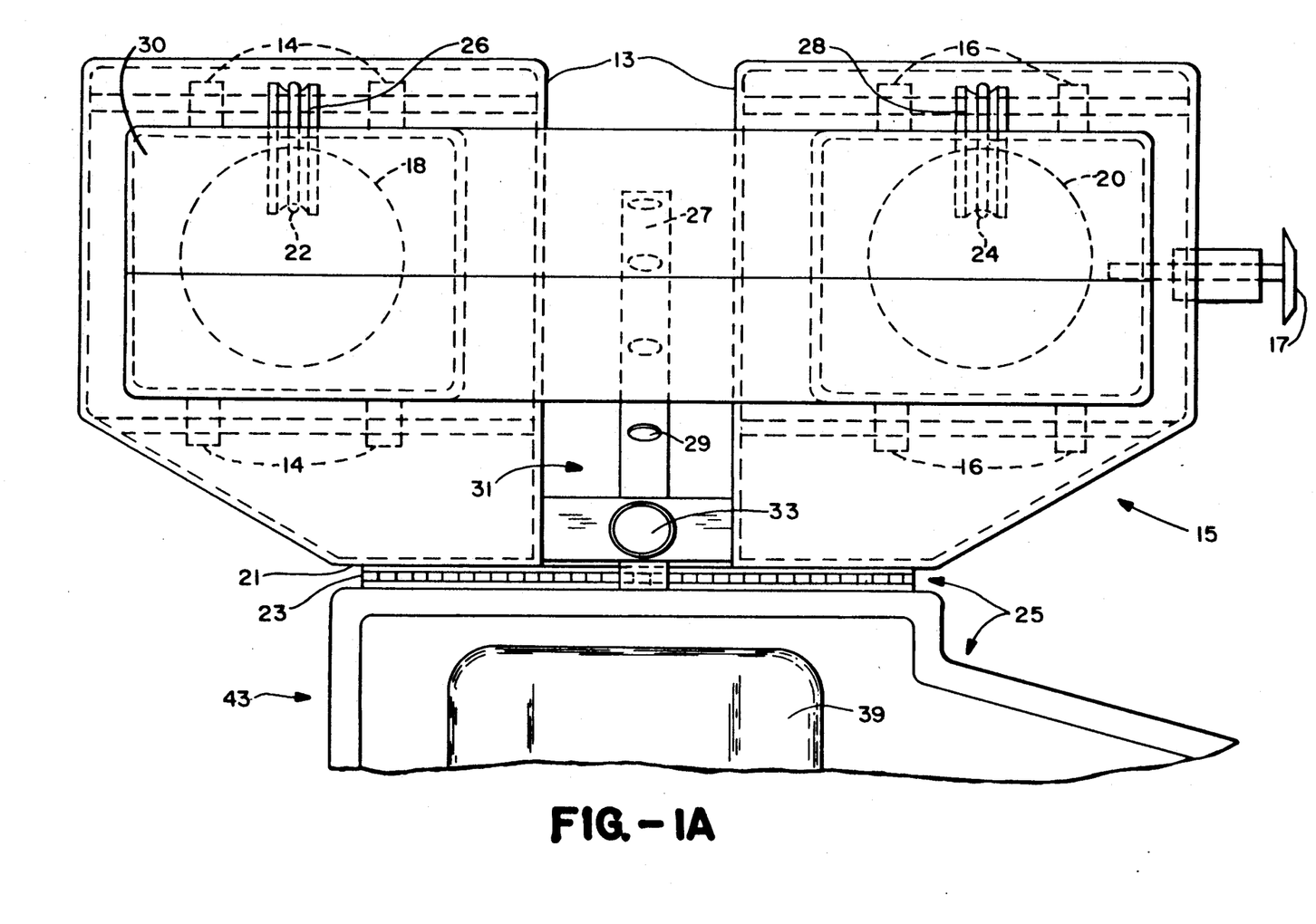
FIG. 1A is a top plan view of the carriage frame for the transducer head showing the transducer head attached thereto and the column roller bearings and counterweights therefor.

Referring now to the drawings, and as best illustrated in FIGS. 1 and 1A, a transducer head 11, which is supported on dual vertical support columns 13 by means of a carriage frame 15, is releasably locked at a desired height position on the support columns by means of a side latch pull mechanism 17 which engages latch pin holes 19 distributed up and down the outside surface of the right-most support column. The height position of the transducer head will be adjusted on this support structure by the operator of the machine to accommodate the patient's body and the test procedure being performed; for ease of adjustment suitable the carriage frame rides over the support columns on bearing wheels 14, 16, and counterweights 18, 20 supported by ropes 22, 24 reeved over pulley wheels 26, 28 are provided in the support columns. The dual support columns are held upright on a suitable base (not shown) and capped by a column cap member 30.

As best shown in FIG. 1A, the transducer head attaches to the front end 21 of the carriage frame 15 by means of a hinge plate 23 mounted across the back wall structure 25 of the transducer head such that the transducer head itself can adjustably be pivoted away from the carriage frame along a horizontal hinge axis. An adjustment strap 27 having a series of spaced latch pin holes 29 and which extends from the back wall structure 25 through a slotted opening 31 in the carriage frame can be engaged by the top latch pull mechanism 33 mounted to the front end of carriage frame. Thus, as further discussed below, the angular position of the various test plane of the head are manually adjustable as well as the vertical positioning of the head itself.

Seen externally, the transducer head is comprised of a somewhat elongated housing 35 having handles 37 attached to each end which can be gripped for raising and lowering the head on the support columns. A first top pressure test pad 39 accessibly projects through a top port 41 formed at the left end 43 of the housing's top wall 45; similarly, a second bottom pressure test pad 47 positioned in direct opposition to the first test pad 39 accessibly projects through a bottom port 49 in the housing's opposed bottom wall 51, and a third front pressure test pad 53 accessibly projects through a front port 55 in and proximate to the end of the housing's front wall 57. Each of the pressure pads has an outwardly facing contact surface 58 having a contoured recess 60 which tends to concentrate pushing forces applied to the pad toward the pad center. This will cause the pushing force on the pads to be in line with the head's internal load cells hereinafter described.

It can be seen that each of the test pads 39, 47, 53 are situated in different test planes generally defined by the housing's top, bottom and front walls 45, 51, 57. These test planes consist of a top or first test plane associated with a downward pushing force applied to the top test pad, that is, a downward force normal to the top plane; a bottom or second test plane associated with an upward force applied against the bottom test pad, that is, an upward force normal to the bottom test plane; and a front vertical test plane associated with a lateral force applied against the front test pad, that is, a lateral force normal to the vertical test plane. Thus, the illustrated transducer provides three pressure test pads which can receive forces applied by different body parts of a human subject normal to three different test planes without pivotal adjustment of the head. Additionally, an optional pull tang 59, which forms a part of a pull device hereinafter described, accessibly projects from the top wall of the housing for measuring pulling forces exerted in muscle test procedures requiring pull strength evaluation.

Referring generally to FIGS. 2-6, three anti-shear arms 61, 63, 65 in the transducer head housing provide the mounting structures for the three different test pads of the transducer head. The first anti-shear arm 61 associated with the top test pad has a distal end in the form of a mounting plate 67 positioned just behind the test pad port 41 in the housing top wall so that the top test pad is mounted directly to this plate accessibly projects through the top port. A relatively broad, U-shaped extender plate 69 extends at an inward angle to connect the proximate end of the first anti-shear arm to the remote end 71 of the housing at a pivot axis 73 which is near the center line of the housing.

Figure 2:
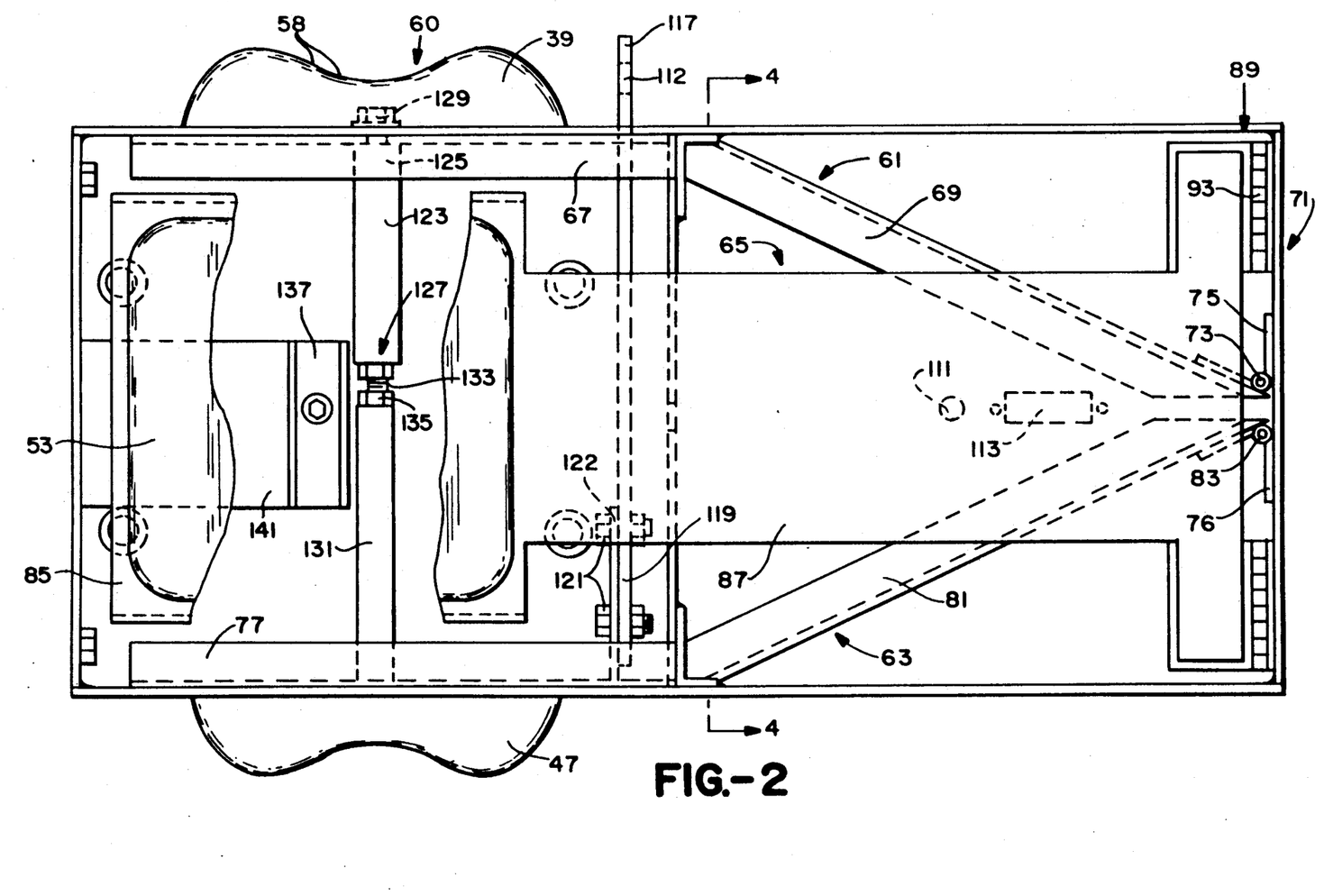
FIG. 2 is a cross-sectional view of the transducer head of FIG. 1 looking in from behind the front wall thereof.

As best seen in FIG. 2, the second anti-shear arm 63 associated with the bottom test pad 47 is substantially a mirror image of the first anti-shear arm 61 and is disposed in the housing in direct opposition to the first anti-shear arm. The test pad mounting plate 77 of the second arm is similarly positioned directly behind the bottom test pad port 49 in the housing's bottom wall 51 so that the bottom test pad accessibly projects from the housing. The inwardly angled extender plate 81 of this arm connects the arm's mounting plate 77 to the remote end of the housing at the second pivot axis 83 located immediately adjacent and parallel to the pivot axis 73 for the first anti-shear arm.

It can generally be seen that the first and second anti-shear arms 61, 63 associated with the top and bottom pressure test pads 39, 47 are generally situated in the parallel test planes associated with these pads. The third anti-shear arm 65 associated with the front test pad 53 is disposed in the transducer housing 35 facing the two first and second anti-shear arms so as to place the third anti-shear arm in a test plane which perpendicularly intersects the parallel test planes of the top and bottom test pads. This third anti-shear arm is comprised of a mounting plate 85 and a straight extender plate 87 connecting the proximate end of the arm to a third pivot axis 89, which is perpendicular to the pivot axis 73, 83 of the other two arms, and which is positioned along the front edge 91 of the remote end 71 of the housing. The mounting plate 85 for this third anti-shear arm is similarly positioned just behind the test port 55 in the front wall of the housing for supporting the front test pad 53 which accessibly projects through this port.

Preferably the pivot axis 73, 83, 89 of each of the anti-shear arms is a hinge axis formed by a laterally stable hinge, such as piano hinges 75, 76, 93 however, it is understood that a hinge axis is not required and that the proximate end of the anti-shear arms could instead be welded directly to the remote end of the housing. With a welded pivot point or other fixed attachment, a certain amount of preloading of the pressure pads is required to overcome the spring tension in the arm.

Figure 3:
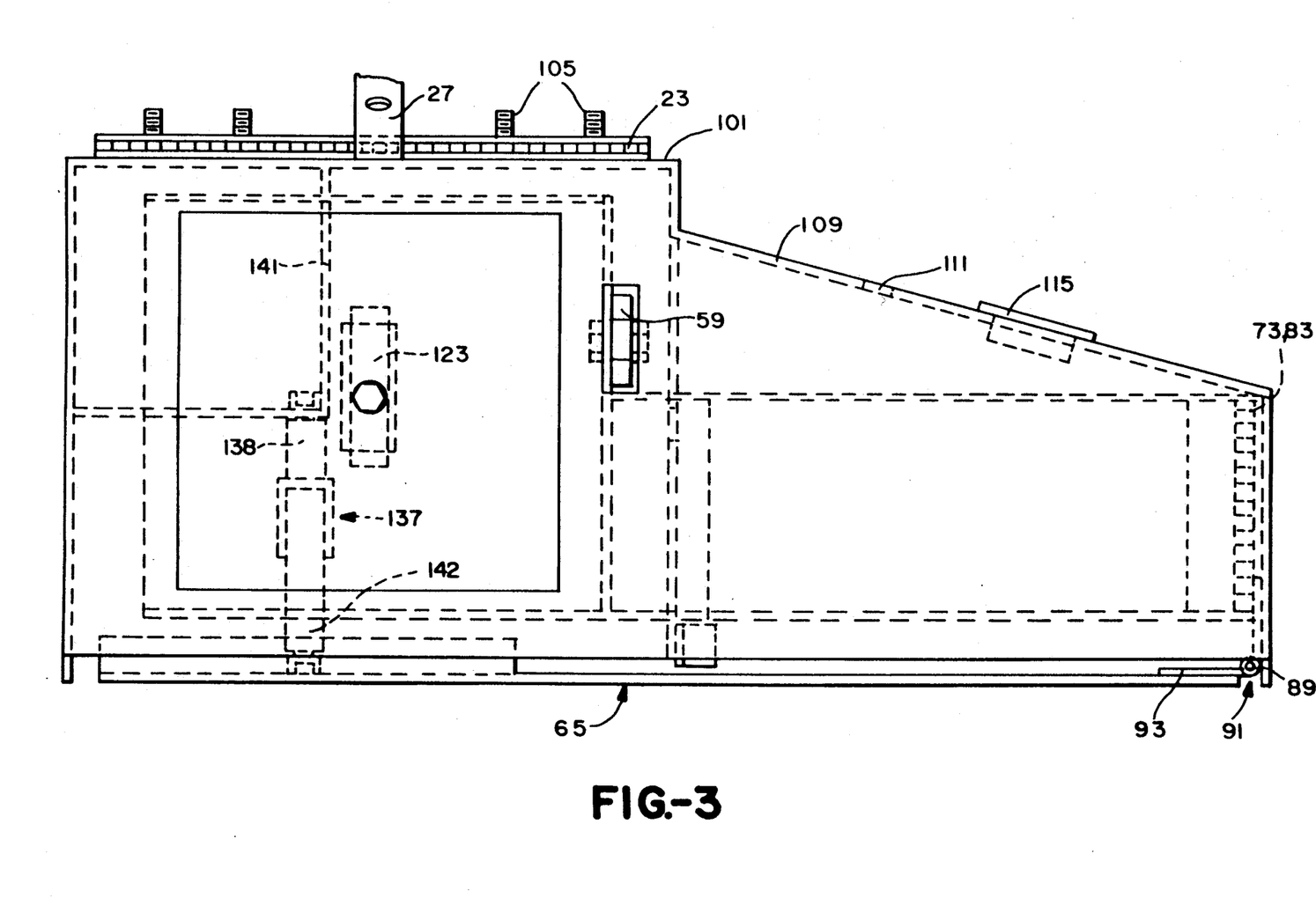
FIG. 3 is a top plan view of the transducer head of FIG. 1 without its front cover.
Figure 4:
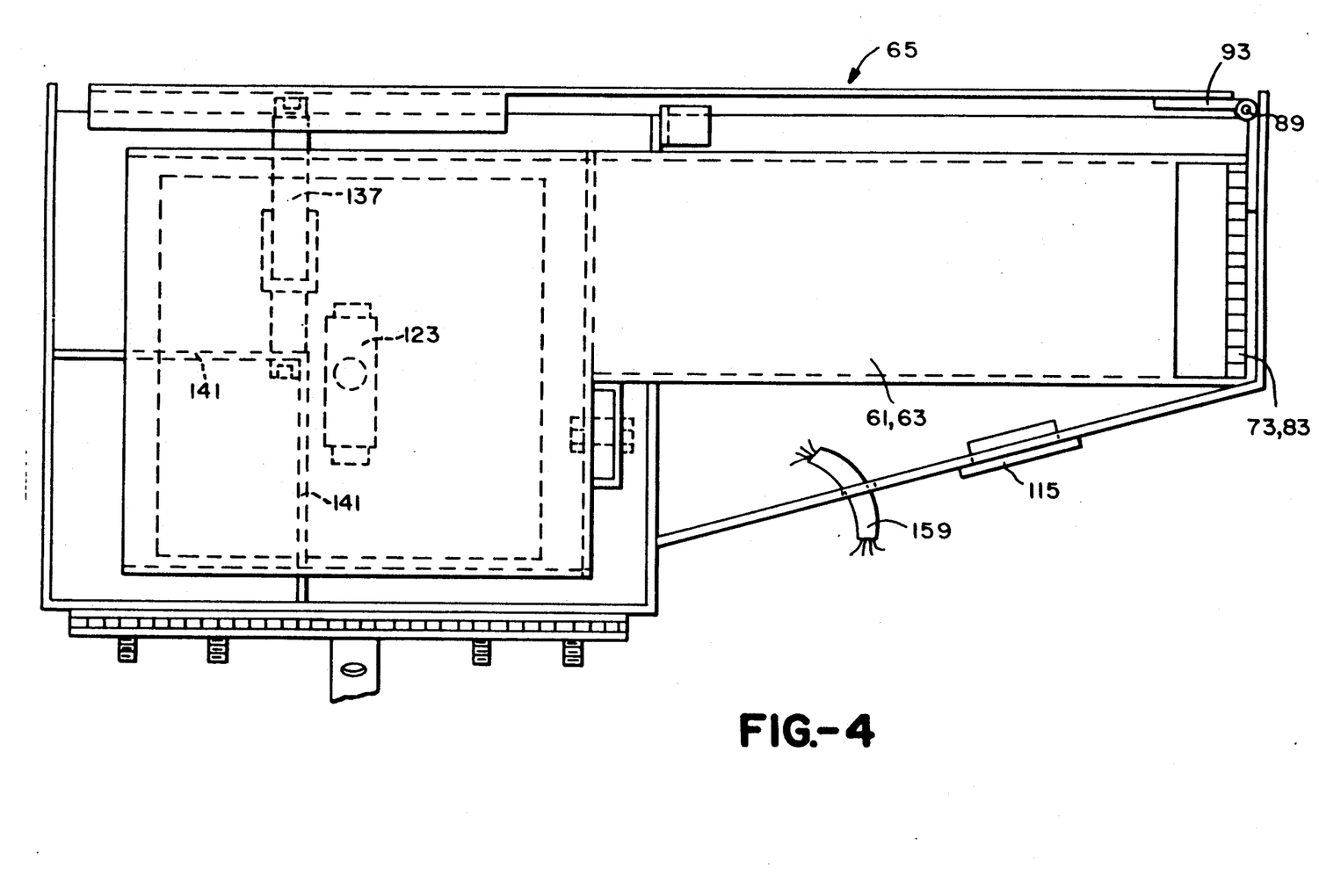
FIG. 4 is a cross-sectional view of the transducer head of claim 1 looking in from behind the bottom wall thereof.
Figure 5:
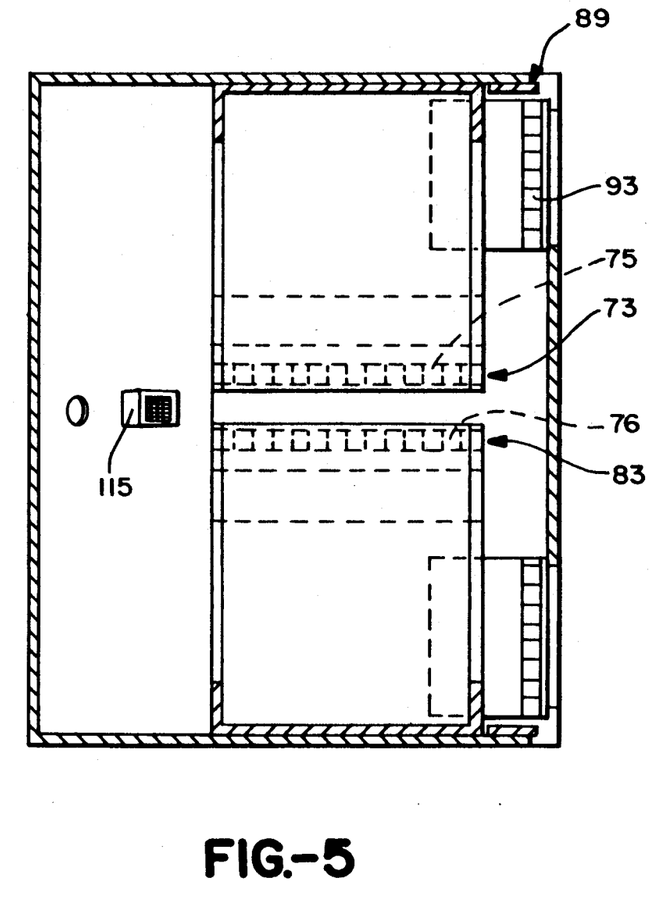
FIG. 5 is a cross-section view thereof taken along lines 4—4 shown in FIG. 2.

FIGS. 3 and 4 generally illustrate the configuration of the transducer housing's back wall structure 25. Viewed from the top or bottom, the transducer housing has more or less a club-shape with a relatively narrow remote end 71 and a left end 43 which has a generally cubed-shape. This back wall structure includes a back mounting wall 101 at the test pad end of the housing to which there is attached a mounting hinge, preferably a piano hinge 103, which, by means of mounting screws 105, hingeably secures the transducer head to the front end 21 of the carriage frame 15. The back wall structure further includes an angled wall portion 109 having a hole 111 for a head wire cable which electrically connects the transducer head to a monitoring device, and a connector plug opening 113 into which a multi-pin auxiliary plug 115 can be suitably mounted for plugging an auxiliary device, such as a grip strength transducer, directly into the head.

The optional pull device of the invention consists of an elongated pull tang 59 having an extended end 117 accessibly projecting through the top wall 45 of the housing, and a base end 119 releasably secured by bolts 121 to a cross-member 122 that upwardly extends from the interior side of the mounting plate 77 of the bottom anti-shear arm 63. A handle (not shown) can easily be attached to the extended end of the pull tang by attaching the handle through the tang eyelet 112. When such a handle is pulled by a patient, a pulling force will be exerted on the anti-shear arm which, like the force applied to the bottom test pad 47, will be normal to the bottom test plane associated with this pad. The pull tang can be added or removed from the transducer head as an optional device by simply bolting or unbolting the pull tang to the cross-member 122. Special calibration of the monitoring device will be required for the pull tang because of the tang's reduced mechanical advantage is compared to the pressure test pads which are further from the pivot axis of the anti-shear arms.

The invention's transducer means located in the transducer head housing 35 includes a first transducer element 123 in the form of a commercially available load cell having a base end 125 and an active contact end 127. The load cell of the first transducer element is attached at its base end to the interior side of the mounting plate 67 of the top anti-shear arm 61 by means of mounting bolt 129, and extends downwardly therefrom toward the mounting plate 77 of the bottom anti-shear arm 63. A buttress rod 131 extends upwardly from the bottom arm mounting plate 77 in opposition to this load cell such that, through the threaded bolt 133 carrying adjustable jam nut 135, the active end 127 of the load cell will contact and react against the extended end 132 of the buttress rod substantially at the center plane of the housing. It is noted that the load cell and buttress rod contact surfaces being on the housing center plane are substantially radially aligned with the pivot axis 73, 83 of the top and bottom anti-shear arms. Such alignment of the load cell with the pivot axis will prevent skewing of the load cell contact surface relative to the reacting end surface of the buttress rod, which otherwise might affect the accuracy of the machine.

Preferably, the lower jam nut of the load cell is adjusted to provide approximately a 1/32" gap between the jam nut and the extended end of the buttress rod when no pressure is applied to either of the top or bottom pressure pads 39, 47. This gap will require a slight displacement of either the top or bottom anti-shear arms before a read-out from the load cell can be obtained. It is found that such a pre-set gap is desirable in obtaining reproducible read-outs from the load cell.

The transducer means further includes a second transducer element 137 responsively attached to the test pad mounting plate 85 of the front anti-shear arm 65 associated with the front test pad 53. Like the first transducer element, this second transducer element consists of a commercially available load cell. The base end 138 of this second load cell is mounted to a load cell mounting bracket 141 which provides a reacting structure for the load cell; the active contact end 142 of the load cell in turn is attached by means of adjustable jam nuts to the mounting plate 85 of the front anti-shear arm 65. It is seen that, unlike the load cell of the first transducer element which is responsive to pressure on the two opposed top and bottom pressure test pads 39, 47, the load cell of this second transducer element is responsive only to pressure applied to the unit's front test pad. It is as seen that the contact surfaces of the active end of this load cell are aligned with the front arm's pivot axis for improved accuracy.

Figure 6:
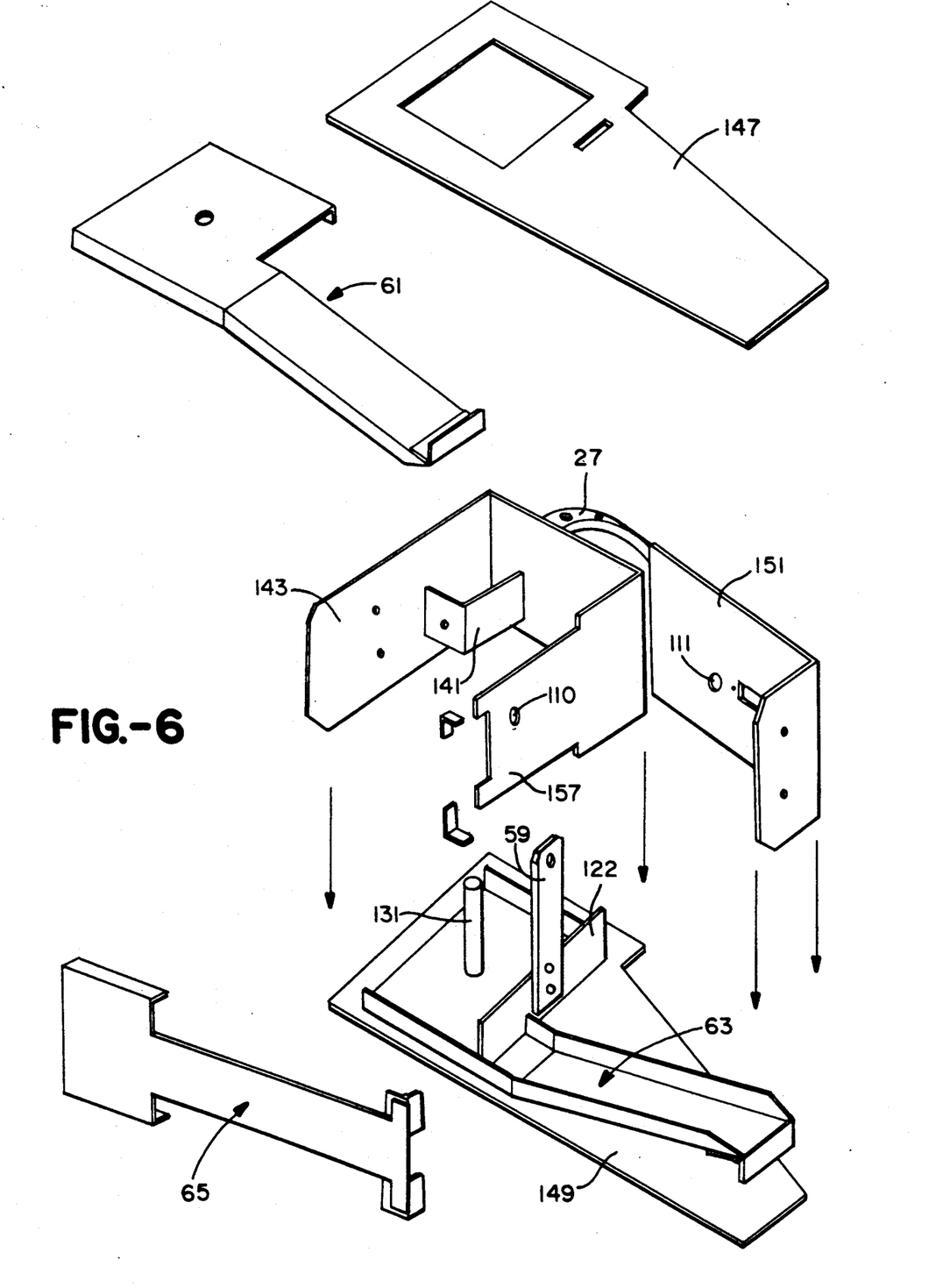
FIG. 6 is an assembly drawing showing the relative positioning of the parts of the illustrated embodiment of the invention.

FIG. 6 of the drawings illustrates the overall assembly of the transducer head of the invention. It is seen that the three anti-shear arms 61, 63, 65 are mounted in a sturdy box support assembly comprised of a U-shaped yoke 143 to which the mounting bracket 141 for the second load cell and the adjustment strap for the transducer head are physically attached, top and bottom reinforcement plates 147, 149 welded to the top and bottom of the yoke to forms the housing's top and bottom walls 45, 47, and an L-shaped back extension wall plate 151 which provides a rearward extension to the yoke and which forms the angled wall position 109 of the housing's back wall structure. This inner box assembly preferably fabricated of a heavy gauge metal, such as 12 gauge steel plate, provides a rigid support structure for the transducer head, and the anti-shear arms and load cells contained therein. Suitable cable wire holes 110, 111 can be provided in the side wall 157 of the yoke and in the back wall extension plate which also has an opening for the accessory plug 115. As shown in FIG. 1, the front and back of the box support assembly can be covered with molded plastic covers which externally form the housing's front wall 57 and is part of the housing's back wall structure 25. Plastic inserts can also be used to cover the housing's top and bottom walls.

Figure 7:
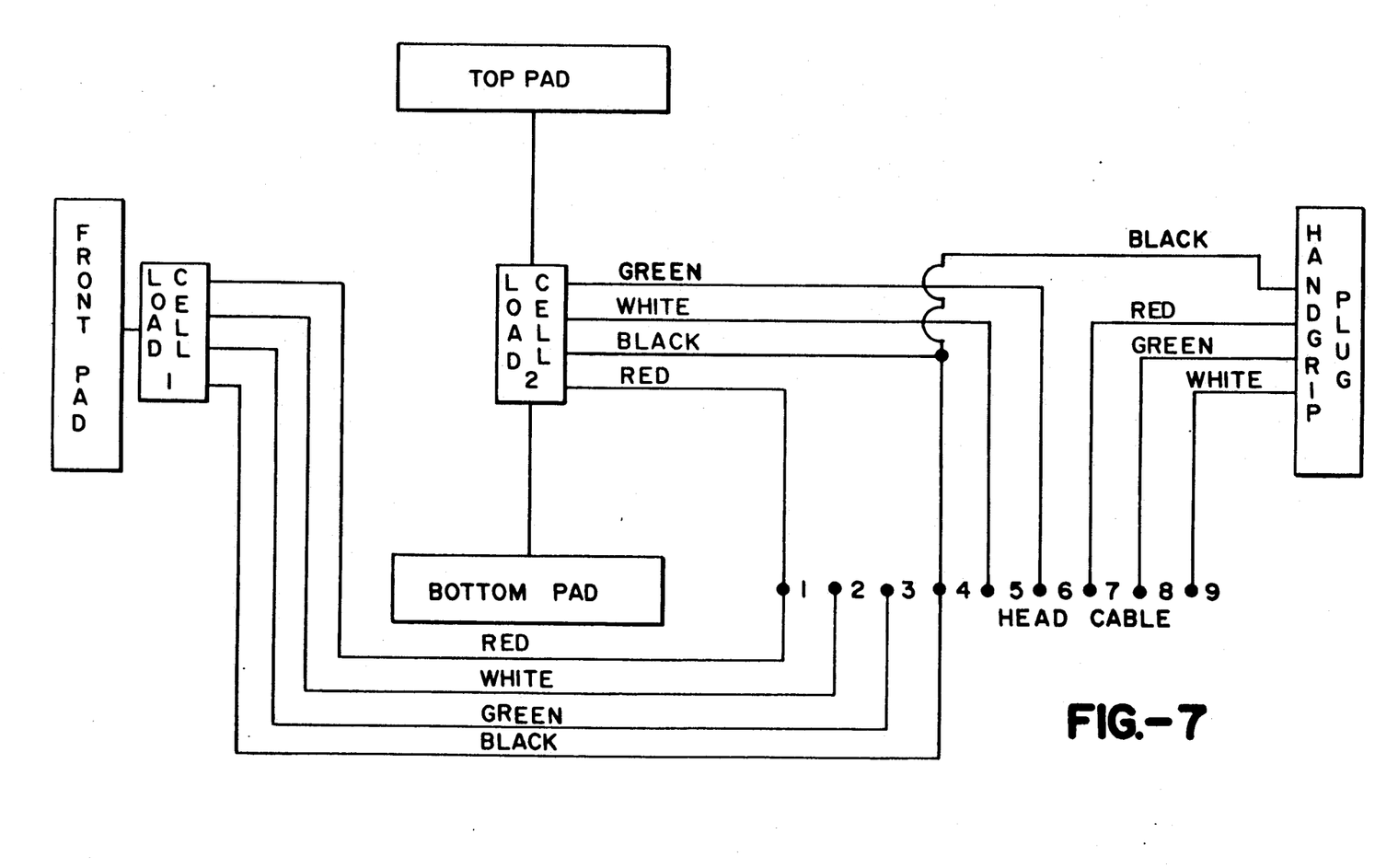
FIG. 7 is a wiring diagram showing the wiring of the load cells of the transducer means in the transducer head housing.

FIG. 7 of the drawings shows a suitable wiring scheme for the load cells for the top, bottom and front pressure test pads 39, 47, 53. Each of the load cells is seen as being wired to a head wire cable 159 (shown in FIG. 4 only) through a conventional wiring scheme having the following conventions:

| Wire Color | Description |
| --- | --- |
| Red | Bias voltage to load cell (and accessory plug) |
| White | Positive side of output signal |
| Green | Negative side of output signal |
| Black | Ground |

As shown, the head cable connections also provide for inputs from an accessory device such as a separate hand grip transducer (not shown) through the accessory plug 115. In this manner, a separate hand grip strength measuring device can be attached directly to the transducer head whereby the electrical signals generated in response to actuation of the hand grip can be sent out to a monitoring device through the same transducer head wire cable used by the load cells contained within the head.

Therefore, it can be seen that the present invention provides a versatile transducer head for a muscle testing apparatus wherein a variety of tests can be performed using the head without the need to readjust the angular position of the head. It can also been seen that a transducer head is provided which is compact in construction, and relatively cost efficient to manufacture. Although the invention has been described in considerable detail in the foregoing specification, it shall be understood that the invention is not intended to be limited by such detail, except as necessitated by the appended claims.

What I claim is:

1. A force transducer head for an isometric testing apparatus for testing the performance of different body parts of a human subject comprising
    at least three accessible pressure test pads,
    a transducer head housing adapted to be adjustably positioned along a support structure,
    mounting structures for holding said test pads in said housing wherein said test pads can be adjusted as a group by positioning said housing along said support structure, said mounting structures being situated to hold each of said test pads in three different test planes associated with said housing including first and second opposed test planes and a third test plane intersecting said two opposed test planes whereby said test pads can receive forces normal to said different test planes applied by different body parts of the subject being tested, and
    transducer means in said housing responsive to a directional pushing force applied to any one of said test pads for generating an electrical output signal proportionate to said applied directional force.

2. The transducer head of claim 1 wherein said transducer means includes a first transducer element and a second transducer element, said second transducer element being responsively connected to the mounting structure associated with test pad in said third intersecting test plane, and said first transducer element being responsively connected between the mounting structures associated with the test pads in said first and second opposed test planes for generating an electrical output signal proportionate to a pushing force to either of the test pads.

3. The transducer head of claim 1 wherein the mounting structure for each of said test pads includes an anti-shear arm having a distal end to which said test pads are mounted and a proximate end attached at a pivot axis within said housing remote from said test pads, and wherein said transducer means are responsive to a force transmitted through said anti-shear arm about the pivot axis thereof.

4. The transducer head of claim 3 wherein said anti-shear arm comprises
    a test pad mounting plate forming the distal end thereof, and
    a relatively broad arm extender plate connecting the test pad mounting plate to the anti-shear arm pivot axis.

5. The transducer head of claim 4 wherein said arm extender plate has a generally U-shape.

6. The transducer head of claim 3 wherein the pivot axis for said anti-shear arm is a hinge axis.

7. The transducer head of claim 6 wherein said hinge axis is comprised of a piano hinge.

8. The transducer head of claim 3 further comprising a pull device having
    a base end secured to one of said anti-shear arms to form a push-pull anti-displacement arm whereby said transducer means is responsive to a pulling force on said pull device as well as to a pushing force on the test pad associated with said push-pull anti-shear arm, and an extended end accessibly projecting from said housing.

9. The transducer head of claim 8 wherein said pull device is releaseably secured to said push-pull anti-shear arm.

10. The transducer head of claim 1 further comprising a pull device accessibly projecting from said housing, said transducer means being responsive to a pulling force against said pull device, as well as to a pushing force against any one of said test pads, for generating an electrical output signal proportionate to said pull force.

11. The transducer head of claim 1 further comprising hinge support means on said transducer housing for adjusting the angular position of said transducer to thereby adjust the angular position of said test planes.

12. The transducer head of claim 11 wherein said hinge support means is disposed along a horizontal axis.

13. A force transducer head for isometric testing apparatus for testing the performance of different body parts of a human subject comprising
at least two pressure test pads,
a transducer housing adapted to be adjustably positioned along a support structure,
a mounting structure within said housing associated with each of said test pads for holding said test pads in said housing to permit said test pads to be adjusted as to group by positioning said housing along said support structure, each of said mounting structure including an anti-shear arm having a distal end to which said test pads are mounted and a proximate end attached at a pivot axis within said housing remote from said test pads, the anti-shear arm of each of said mounting structures being situated to hold its associated test pad in a different test plane whereby said test pads can receive forces normal to said different test planes applied by different body parts of the subject being tested, and
a transducer element connected to each of said anti-shear arms, each of said transducer elements being so connected as to be responsive to a force transmitted through said anti-shear arms about the pivot axis thereof whereby a directional pushing force applied to any one of said test pad causes an associated transducer element to generate an electrical output signal proportionate to said pushing force.

14. The transducer head of claim 13 wherein said anti-shear arms are situated in opposed relation and said transducer is responsively connected between said anti-shear arms for generating an electrical output signal proportionate to a pushing force to either of the test pads associated with said opposed anti-shear arms.

15. The transducer head of claim 14 wherein
each of said anti-shear arms includes a test pad mounting plate forming the distal end thereof and a relatively broad arm extender plate connecting the test pad mounting plate to the arm pivot axis, and
said transducer element is connected between the mounting plates of said opposed anti-shear arms.

16. The transducer head of claim 15 wherein the transducer element associated with said opposed anti-shear arms is so connected that a slight incremental displacement of said opposed arms must occur before responsive contact with said transducer element is made by a pushing force on one of the associated test pads 17. The transducer head of claim 13 wherein said pressure test pads include an outwardly facing contact surface having a contoured recess which tends to concentrate the pushing force thereon toward the center of the pad.

18. A force transducer head for an isometric testing apparatus for testing the performance of different body parts of a human subject comprising
at least three pressure test pads,
a transducer housing having a top wall and a bottom wall generally defining two opposed substantially parallel first and second test planes and a front wall generally defining a third test plane intersecting and being substantially perpendicular to said opposed test planes, each of said pressure test pads being disposed in a different one of said housing walls so as to receive forces normal to said different test planes applied by different body parts of the subject being tested,
a test pad mounting structure within said housing associated with each of said test pads, each of said mounting structures including an anti-shear arm having a distal end to which said test pads are mounted and a proximate end attached at a pivot axis within said housing remote from said test pads, the anti-shear arm of each of said mounting structures being situated to hold its associated test pad in a different one of said intersecting test planes, and
transducer means in said housing responsive to a force transmitted through said anti-shear arms about the pivot axis thereof whereby a directional pushing force applied to any one of said test pads causes said transducer means to generate an electrical output signal proportionate to said pushing force.

19. The transducer head of claim 18 wherein said transducer means includes a first transducer element and a second transducer element, said second transducer element being responsively connected to the anti-shear arm associated with the test pad in said third intersecting test plane, and said first transducer element being responsively connected between the anti-shear arms associated with the test pads in said first and second opposed test planes, said first transducer element generating an electrical output signal proportionate to a pushing force to either one of the test pads associated with said opposed anti-shear arms.

20. The transducer head of claim 18 further comprising a pull device having
a base end secured to one of said arms to form a push-pull arm whereby said transducer means is responsive to a pulling force on said pull device as well as to a pushing force on the test pad associated with said push-pull arm, and
an extended end accessibly projecting from said housing.

21. The transducer head of claim 20 wherein the extended end of said pull device projects from the top wall of said housing.

22. The transducer head of claim 21 wherein the base end of said pull device is secured to the arm associated with the test pad in said housing bottom wall.

23. The transducer head of claim 19 wherein each of said transducer elements has an active contact end with a contact surface which is substantially radially aligned with the pivot axis of the anti-shear arms associated with said transducer elements.

* * * * *